United States Patent [19]
Wos et al.

[11] Patent Number: 6,048,895
[45] Date of Patent: Apr. 11, 2000

[54] AROMATIC C16-C20 SUBSTITUTED TETRAHYDRO PROSTAGLANDINS USEFUL AS FP AGONISTS

[75] Inventors: John August Wos, Cincinnati; Mitchell Anthony deLong, West Chester; Jack S. Amburgey, Jr., Loveland, all of Ohio; Haiyan George Dai, Drexel Hill, Pa.; Biswanath De, Cincinnati; David Lindsey Soper, Monroe, both of Ohio

[73] Assignee: The Procter & Gamble Company, Cincinnati, Ohio

[21] Appl. No.: 09/148,538

[22] Filed: Sep. 4, 1998

Related U.S. Application Data
[60] Provisional application No. 60/058,252, Sep. 9, 1997.

[51] Int. Cl.⁷ .......................... A61K 31/215; C07C 69/76
[52] U.S. Cl. .......................... 514/530; 514/568; 514/573; 514/617; 514/618; 514/619; 514/620; 514/561; 514/381; 514/445; 548/252; 549/65; 549/66; 560/11; 560/40; 560/60; 560/61; 562/426; 562/429; 562/472; 562/503; 564/162
[58] Field of Search .................................... 562/426, 429, 562/472, 503; 514/561, 568, 573, 530, 617, 618, 619, 620, 381, 445; 560/11, 40, 60, 61; 564/162, 165, 171; 548/252; 549/65, 66

[56] References Cited

U.S. PATENT DOCUMENTS

| | | | |
|---|---|---|---|
| 3,776,938 | 12/1973 | Bergstrom et al. | 260/468 |
| 3,966,792 | 6/1976 | Hayashi et al. | 260/468 |
| 4,004,020 | 1/1977 | Skuballa et al. | 424/278 |
| 4,011,262 | 3/1977 | Hess et al. | 260/520 B |
| 4,024,179 | 5/1977 | Bindra et al. | 260/473 A |
| 4,051,238 | 9/1977 | Sokolowski | 424/181 |
| 4,073,934 | 2/1978 | Skuballa et al. | 424/305 |
| 4,128,720 | 12/1978 | Hayashi et al. | 560/9 |
| 4,154,950 | 5/1979 | Nelson | 560/53 |
| 4,206,151 | 6/1980 | Grudzinskas | 568/367 |
| 4,621,100 | 11/1986 | Lund et al. | 514/573 |
| 5,166,178 | 11/1992 | Ueno et al. | 514/573 |
| 5,212,324 | 5/1993 | Ueno | 554/118 |
| 5,296,504 | 3/1994 | Stjernschantz et al. | 514/530 |
| 5,302,617 | 4/1994 | Ueno | 514/573 |
| 5,321,128 | 6/1994 | Stjernschantz et al. | 514/530 |
| 5,332,730 | 7/1994 | Chan | 511/151 |
| 5,409,911 | 4/1995 | Tyler et al. | 514/91 |
| 5,422,368 | 6/1995 | Stjernschantz | 514/530 |
| 5,422,369 | 6/1995 | Stjernschantz | 514/530 |
| 5,426,115 | 6/1995 | Ueno et al. | 514/438 |
| 5,578,618 | 11/1996 | Stjernschantz et al. | 514/365 |
| 5,587,391 | 12/1996 | Burk | 514/357 |
| 5,627,208 | 5/1997 | Stjernschantz et al. | 514/530 |
| 5,665,773 | 9/1997 | Klimko et al. | 514/530 |
| 5,688,819 | 11/1997 | Woodward et al. | 514/357 |
| 5,703,108 | 12/1997 | Cameron et al. | 514/382 |
| 5,834,498 | 11/1998 | Burk | 514/445 |

FOREIGN PATENT DOCUMENTS

| | | |
|---|---|---|
| 0 857 718 A1 | 6/1997 | European Pat. Off. |
| 002460990 | 7/1976 | Germany. |
| 1 456 838 | 11/1972 | United Kingdom. |
| 1 542 569 | 8/1976 | United Kingdom. |
| WO 92/02495 | 2/1992 | WIPO. |
| WEO 95/18102 | 7/1995 | WIPO. |
| WO 97/23225 | 7/1997 | WIPO. |
| WO 97/31895 | 9/1997 | WIPO. |
| WO 98/12175 | 3/1998 | WIPO. |
| WO 98/20880 | 5/1998 | WIPO. |
| WO 98/20881 | 5/1998 | WIPO. |
| WO 98/21180 | 5/1998 | WIPO. |
| WO 98/50024 | 11/1998 | WIPO. |

OTHER PUBLICATIONS

Liljebris, C., Selen. G., Resul, B., Stjernschantz, J., and Hacksell, U., "Dervatives of 17–Phenyl–18, 19,20–trinor-prostaglandin $F_{2\alpha}$ Isopropyl Ester: Potential Antiglaucoma Agents", *Journal of Medicinal Chemistry*, vol. 38, No. 2, (1995).

Bundy, G. L., and Lincoln, F. H., "Synthesis of 17–Phenyl–18, 19–20–Trinoprostaglandins I. the $PG_1$, Series", *Prostaglandins*, vol. 9, No. 1, (Jan. 1975).

*Primary Examiner*—Joseph McKane
*Attorney, Agent, or Firm*—James C. Kellerman; Carl J. Roof; David L. Suter

[57] ABSTRACT

The invention provides novel PGF analogs. In particular, the present invention relates to compounds having a structure according to the following formula:

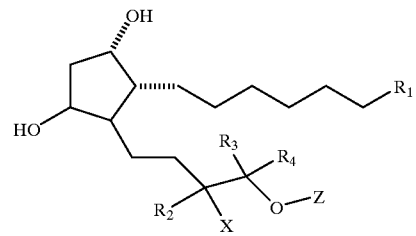

wherein $R_1$, $R_2$, $R_3$, $R_4$, X, and Z are as defined.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

24 Claims, No Drawings

AROMATIC C16-C20 SUBSTITUTED TETRAHYDRO PROSTAGLANDINS USEFUL AS FP AGONISTS

CROSS REFERENCE

This application claims priority under Title 35, United States Code 119(e) from Provisional Application Ser. No. 60/058,252, filed Sep. 9, 1997.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_{2\alpha}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2\alpha}$ has the following formula:

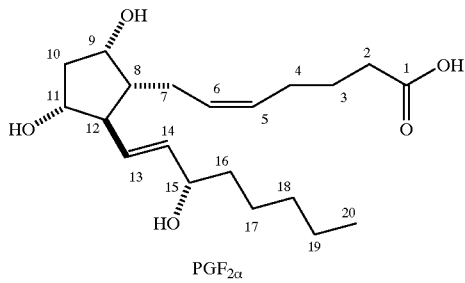

$PGF_{2\alpha}$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandins*, Vol. 9 No. 1 (1975), pp. 1–4; W. Bartman, G. Beck, U. Lerch, H. Teufel, and B. Scholkens, "Luteolytic Prostaglandins: Synthesis and Biological Activity", *Prostaglandins*, Vol. 17 No. 2 (1979), pp. 301–311; C. Iiljebris, G. Selen, B. Resul, J. Sternschantz, and U. Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits some of the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_{2\alpha}$ has also been shown to be a stimulator of bone resorption but not as potent as $PGE_2$. Also, it has been demonstrated the $PGF_{2\alpha}$ has little effect on bone formation. It has been suggested that some of the effects of $PGF_{2\alpha}$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

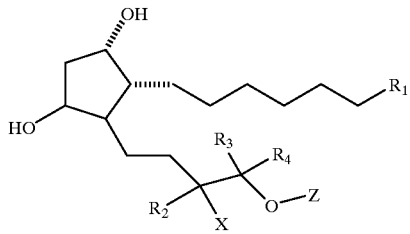

wherein $R_1$, $R_2$, $R_3$, $R_4$, X, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using these compounds or the compositions containing them.

DETAILED DESCRIPTION OF THE INVENTION

Terms and Definitions

"Acyl" is a group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred alkyl are unsubstituted. Preferred substituted alkyl are mono-, di-, or trisubstituted. Preferred alkyl substituents include halo, haloalkyl, hydroxy, aryl (e.g., phenyl, tolyl, alkyloxphenyl, alkyloxycarbonylphenyl, halophenyl), heterocyclyl, and heteroaryl.

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to about 4 substituents on the ring. Preferred aromatic ring substituents include: halo, cyano, alkyl, heteroalkyl, haloalkyl, phenyl, phenoxy or any combination thereof. More preferred substituents include halo and haloalkyl. Preferred aromatic rings include naphthyl and phenyl. The most preferred aromatic ring is phenyl.

"Bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to about 4 substituents on the ring. Preferred carbocyclic aliphatic ring substituents include: halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl. The most preferred carbocyclic aliphatic ring is cycloheptyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents. Preferred heteroalkyl are unsubstituted. Preferred heteroalkyl substituents include halo, hydroxy, aryl (e.g., phenyl, tolyl, alkyloxphenyl, alkyloxycarbonylphenyl, halophenyl), heterocyclyl, and heteroaryl. For example, alkyl substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- $C_1$–$C_3$ alkanylamino, methylphenylamino, methylbenzylamino, $C_1$–$C_3$ alkanylamido, carbamamido, ureido, guanidino).

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, alkyl, heteroalkyl, haloalkyl, phenyl, phenoxy or any combination thereof. More preferred substituents include halo and haloalkyl. Preferred heterocyclic aliphatic rings include piperzyl, morpholinyl, tetrahydrofuranyl, tetrahydropyranyl and piperdyl.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 member atoms in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, alkyl, heteroalkyl, haloalkyl, phenyl, phenoxy or any combination thereof. More preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Hydroxyalkyl" means HO-alkyl.

"Lower alkyl" is an alkyl chain radical comprised of 1 to 6, preferably 1 to 4 carbon atoms.

"Phenyl" is a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, alkyl, heteroalkyl, haloalkyl, phenyl, phenoxy or any combination thereof. More preferred substituents on the phenyl ring include halo and haloalkyl. The most preferred substituent is halo. The preferred substitution pattern on the phenyl ring is ortho or meta. The most preferred substitution pattern on the phenyl ring is ortho.

Compounds

The subject invention involves compounds having the following structure:

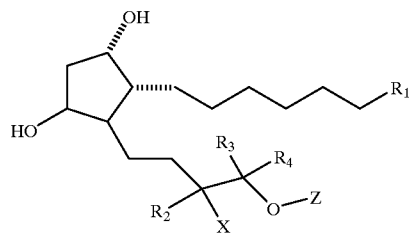

In the above structure, $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring. Preferred $R_5$ is $CH_3$, $C_2H_5$, $C_3H_7$. Preferred $R_1$ is $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$. More preferred $R_1$ is $CO_2H$, $C(O)NHOH$, $CO_2CH_3$, and $CO_2C_3H_5$. Most preferred $R_1$ is $CO_2H$ and $CO_2CH_3$.

In the above structure, $R_2$ is H or lower alkyl. Preferred $R_2$ is H and $CH_3$. Most preferred $R_2$ is H.

In the above structure, X is $NR_6R_7$, $OR_8$, $SR_9$, $S(O)R_9$, $S(O)_2R_9$, or F; wherein $R_6$, $R_7$ and $R_8$ are selected independently from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring. Preferred $R_6$ and $R_7$ are H, $CH_3$ and acyl. Preferred $R_8$ is H, $CH_3$, $CH_2CH_2OH$. Preferred $R_9$ is $CH_3$ and $CH_2CH_2OH$. Preferred X is $NR_6R_7$ and $OR_8$. Most preferred X is OH.

In the above structure, $R_3$ and $R_4$ are independently H, alkyl, hydroxyalkyl, alkoxyalkyl, $OR_{10}$, or $SR_{10}$, except that both $R_3$ and $R_4$ are not H; wherein $R_{10}$ is alkyl, heteroalkyl, carbocyclic aliphatic ring, heterocyclic aliphatic ring, aromatic ring, or heteroaromatic ring. $R_{10}$ has from 1 to about 8 member atoms. Preferred $R_3$ is H and $CH_3$. Preferred $R_4$ is H and $CH_3$. Preferred $R_{10}$ is $CH_3$.

In the above structure, Z is carbocyclic aliphatic ring, heterocyclic aliphatic ring, aromatic ring, or heteroaromatic ring. Preferred Z is monocyclic carbocyclic aliphatic ring, monocyclic heterocyclic aliphatic ring, monocyclic aromatic ring and monocyclic heteroaromatic ring. More preferred Z is monocyclic aromatic ring and monocyclic heteroaromatic ring. The most preferred Z is thienyl or phenyl.

The invention also includes optical isomers, diastereomers and enantiomers of the above structure. Thus, at all stereocenters where stereochemistry is not defined ($C_{11}$, $C_{12}$, $C_{15}$, and $C_{16}$), both epimers are envisioned. Preferred stereochemistry at all such stereocenters of the compounds of the invention mimic that of naturally occurring $PGF_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. Iiljebris, G. Selen, B. Resul, J. Sternschantz, and U. Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. Particularly preferred syntheses include the following two general reaction schemes:

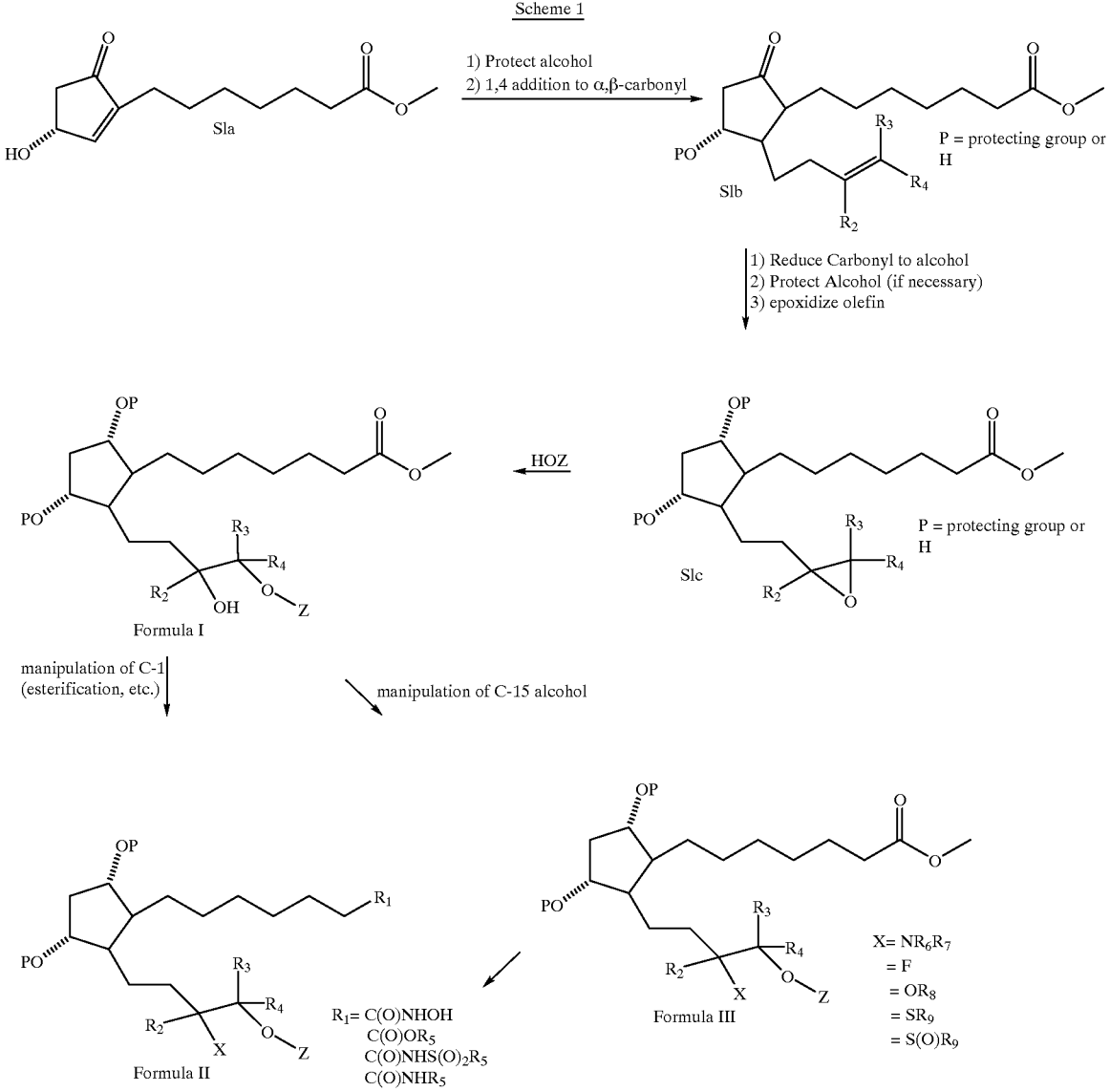

Scheme 1

In Scheme 1, $R_1$, $R_2$, $R_3$, $R_4$, X, and Z are as defined above. The Methyl 7[3-(R)-hydroxy-5-oxo-1-cyclopent-1-yl] heptanoate (S1a) depicted as starting material for Scheme 1 is commercially available (such as from the Sumitomo Chemical Company, Tokyo, Japan or the Cayman Chemical Company, Ann Arbor, Mich.).

In the above Scheme 1, Methyl 7[3-(R)-hydroxy-5-oxo-1-cyclopent-1-yl] heptanoate (S1a) is protected, preferably as a silyl ether, and is subjected to conditions which result in a 1,4 addition reaction of a suitably-substituted carbon nucleophile. For example, a cuprate addition of a homo-allyl alkene may be used. These manipulations result in ketones of the type depicted by S1b, which are readily reduced to alcohols, preferably with a boron reducing agent. These alcohols can be protected if needed during further manipulations. These manipulations are followed by the epoxidation of the olefin with a mild epoxidizing agent, such as meta chloroperbenzoic acid, to give compounds of the type depicted by S1c. These epoxides are reacted with oxygen nucleophiles under a great variety of conditions, but especially in the presence of Lewis acids, to create compounds depicted by Formula I. Examples 4 and 5 illustrate compounds of Formula I.

Compounds depicted by Formula II are readily made from compounds of Formula I by their reaction with known ester manipulating reagents. For example, hydroxylamine transforms the ester functionality into a hydroxamic acid and LiOH transforms the ester to an acid. Examples 1–3 and 13–16 illustrate compounds of Formula II.

To create compounds depicted by Formula III, (Illustrated by Example 20) compounds are treated with a variety of agents known to transform secondary alcohols into halides, ethers, amines, sulfides and sulfoxides. Such reactions are disclosed, for example, in *Advanced Organic Chemistry*, by Jerry March. The compounds of Formula III may then be subsequently transformed at $C_1$ into the compounds depicted by Formula II, using substantially the same method for transforming the compounds of Formula I into the compounds depicted by Formula II.

Scheme 2

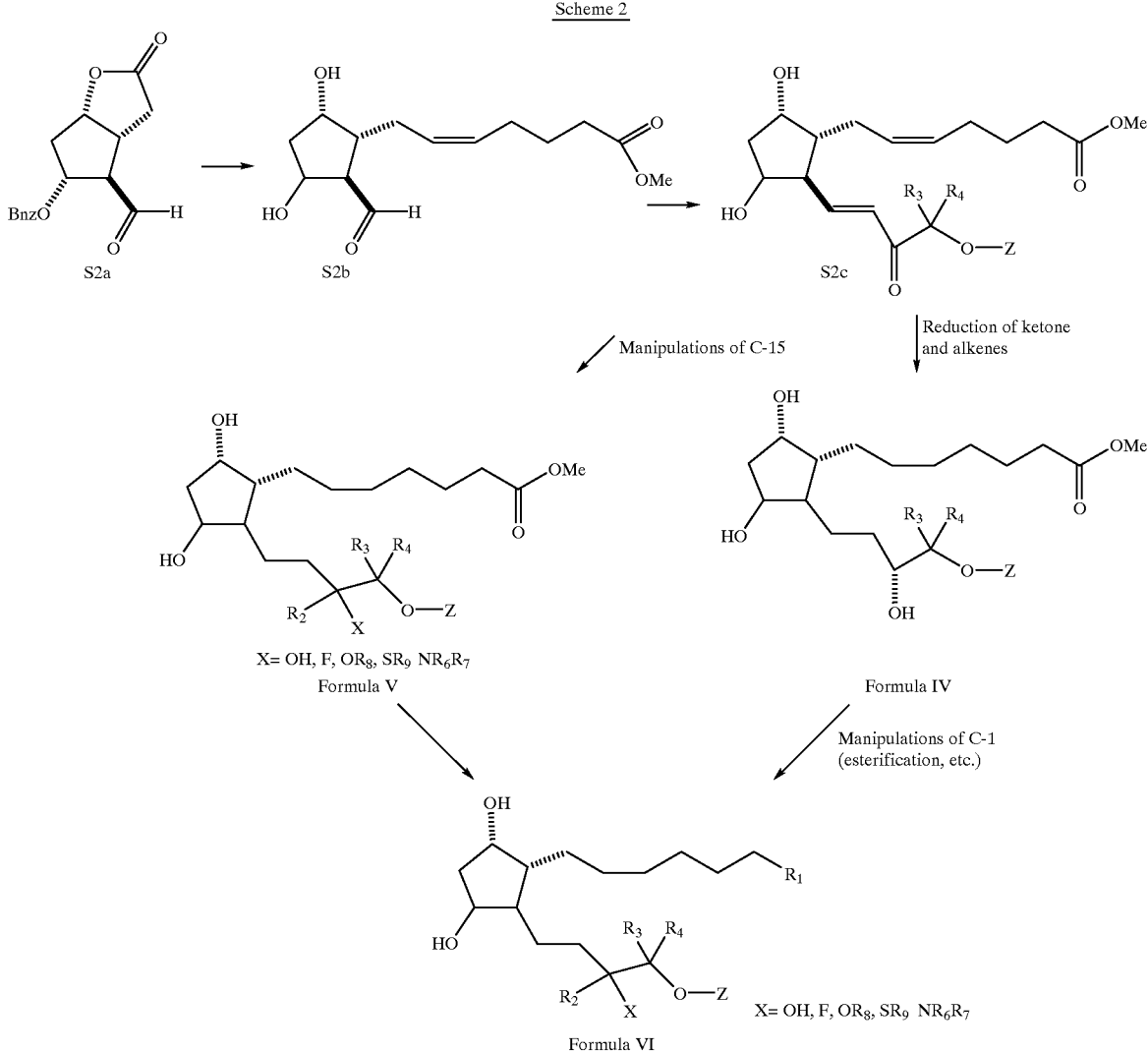

In Scheme 2, $R_1$, $R_2$, $R_3$, $R_4$, X, and Z are as defined above. The Corey lactone (S2a) depicted as starting material for Scheme 2 is commercially available (such as from the Sumitomo Chemical Company, Tokyo, Japan; or the Cayman Chemical Company, Ann Arbor, Mich.).

Compounds depicted by Formula IV are made by elaboration of the commercially-available Corey lactone (S2a) to the advanced intermediate S2b. (An example of such a reaction is found in Example 6 herein). The intermediate S2b is coupled with beta-keto phosphonates, or the alcohols are suitably protected and olefination reactions are effected to give compounds of the type depicted by S2c after deprotection of the alcohol if appropriate. These compounds then undergo reduction of the alkenes and the ketone to give the compounds depicted by Formula IV. Example 12 illustrates a compound of Formula IV.

Compounds depicted by Formula V are derived from compounds of S2c by suitably protecting the alcohols, addition of $R_2$, if desired, and reduction of the ketone and alkenes followed by suitable functional group manipulations as described above in Scheme 1. Examples 25, 26, and 28 illustrate compounds of Formula V.

Compounds depicted by Formula VI may be made from either compounds of Formula IV or Formula V, by reaction of the $C_1$ ester as described above in Scheme 1. Examples 6–11, 17 and 18, 22–24, 27, and 29–31 illustrate compounds of Formula VI.

These compounds are isolated by methods known to one of ordinary skill in the art. Such methods include, but are not limited to, extraction, solvent evaporation, distillation, and crystallization.

The following non-limiting examples illustrate the compounds, compositions, and uses of the present invention.

EXAMPLES

Compounds are analyzed using $^1H$ and $^{13}C$ NMR, Elemental analysis, mass spectra, high resolution mass spectra and/or IR spectra as appropriate.

Typically, inert solvents are used, preferably in anhydrous form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh;

Baker) and visualized using UV, 5% phosphomolybdic acid in EtOH, or ammonium molybdate/ceric sulfate in 10% aqueous $H_2SO_4$.
Example 1
Preparation of 13,14-dihydro-16,16-dimethyl-16-(2-fluorophenoxy) 16-tetranor-prostaglandin $F_1\alpha$
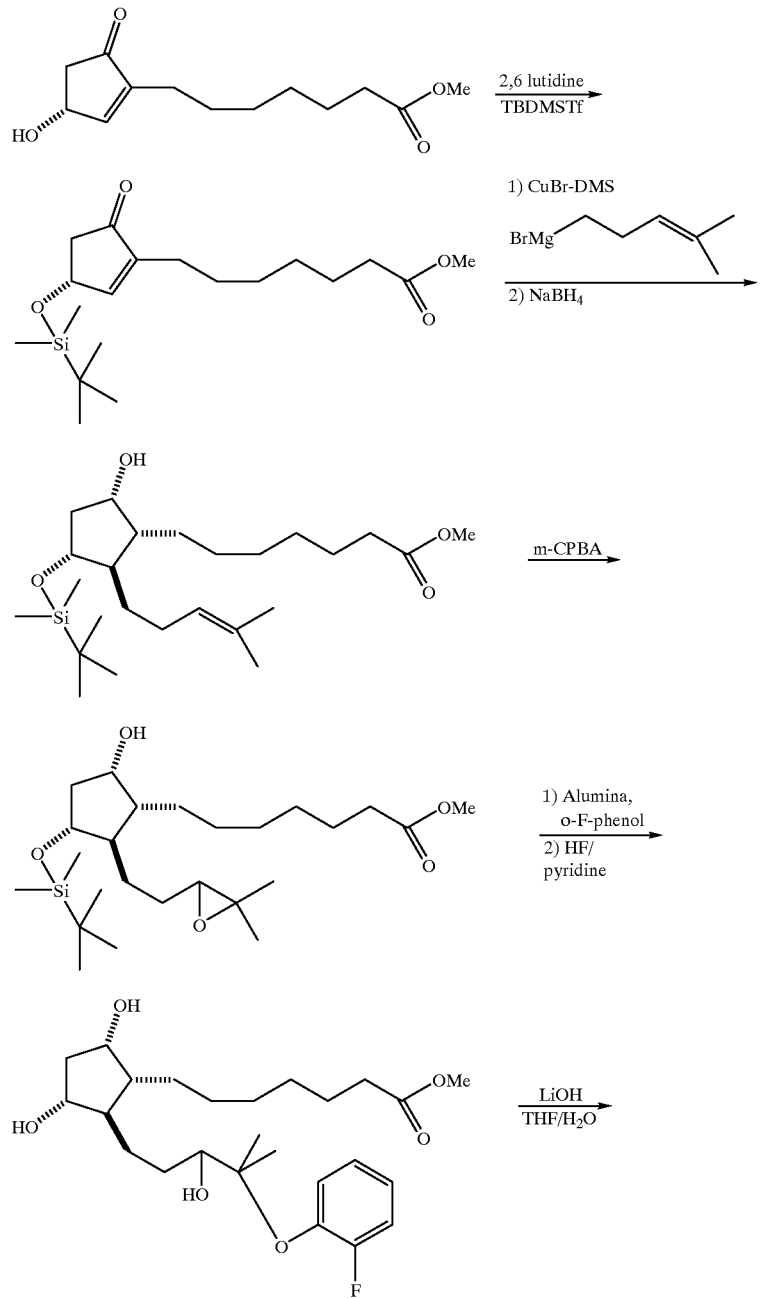

-continued

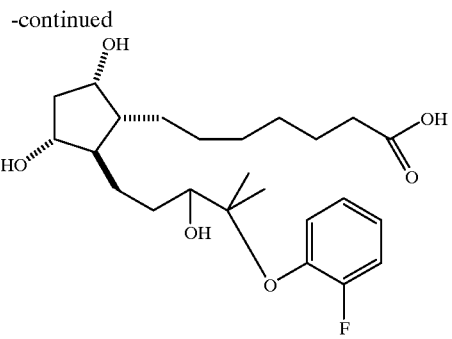

a.

Methyl 7-(2-oxo-4-(1,1,2,2-tetramethyl-1-silapropoxy)cyclopent-1-enyl) heptanoate To a solution of Methyl-7-[3-(R)-hydroxy-5-oxo-1-cyclopenten-1-yl] heptanoate (1 equiv.) in $CH_2Cl_2$ at −78° C. is added 2,6 lutidine (1.3 equiv.) dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 1% HCl is added until the solution is pH<5.0 and the layers are separated. The water layer is back-extracted with $CH_2Cl_2$ and the organic layers are combined. The organic layer is washed with brine, dried ($Na_2SO_4$) and concentrated. The residue is distilled under vacuum (10 mm Hg) to provide the silyl ether.

b.

Methyl 7-(5-(4-methyl-pent-3-enyl)-2-hydroxy-4-(1,1,2,2-tetramethyl-1-silapropoxy)cyclopentyl) heptanoate To a slurry of $Mg^O$ powder (2 equiv.) in THF at room temperature is added one crystal of $I_2$ and 1-bromoisoprene (2 equiv.) dropwise over 10 minutes. The reaction is exothermic as the addition continues. After the addition is complete, the reaction is refluxed for 3 hours and cooled to room temperature. The Grignard is diluted with THF and is added via cannula to a 3-necked flask equipped with mechanical stirring and is charged with CuBr as the dimethyl sulfide adduct (DMS) (2 equiv.) in a 1:1 solution of THF/DMS at −78° C. After the addition of the Grignard reagent (~20 minutes), the reaction is stirred for 1 hour at −78° C. A solution of the ketone (1 equiv.) in THF is then added dropwise over 25 minutes. The reaction is stirred at −78° C. for 15 minutes then allowed to warm slowly to room temperature over 2 hours. The reaction is quenched with aqueous $NH_4Cl$ and the excess DMS allowed to evaporate. The reaction is partitioned between brine and $CH_2Cl_2$ and the layers are separated. The aqueous layer is back-extracted with $CH_2Cl_2$ and the organic layers are combined and dried ($Na_2SO_4$). The solvent is removed in vacuo and the residue chromatographed on $SiO_2$ (10% hexane/EtOAc) to give the ketone as a clear oil.

The ketone is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and $CH_2Cl_2$ and the layers separated. The aqueous layer is back-extracted with $CH_2Cl_2$ and the organic layers combined and dried ($Na_2SO_4$). The solvent is removed in vacuo and the residue is chromatographed on $SiO_2$ (30% EtOAc/hexanes) to give the alcohol as a colorless oil.

c.

Methyl 7-(2-hydroxy-5-(2-(3,3-dimethyl(2-oxiranyl)ethyl)-4-(1,1,2,2-tetramethyl-1-silapropoxy)cyclopentyl)heptanoate The alcohol (1 equiv.) is dissolved in $CH_2Cl_2$ and cooled to 0° C. Sodium bicarbonate is added, followed by m-CPBA (57%–85% purity) (3 equiv.) portionwise over 15 minutes. After the addition is complete, the reaction is stirred for 20 hours at room temperature. The reaction is poured onto water, partitioned between brine and $CH_2Cl_2$ and the layers are separated. The aqueous layer is back-extracted with $CH_2Cl_2$ and the organic layers are combined and dried ($Na_2SO_4$). The solvent is removed in vacuo and the residue is chromatographed on $SiO_2$ (20% EtOAc/hexanes) to give the pair of epoxide diastereomers.

d.

13,14-dihydro-16,16 dimethyl, 16-(2-fluorophenoxy)-16-tetranor prostaglandin $F_1\alpha$ methyl ester In a round bottom flask, epoxide (1 equiv.) and dry toluene are placed, the flask is cooled to 0° C. and then treated with 2-fluorophenol (1.2 eq) and Alumina (1 g per 100 mg of phenol). The ice bath is removed and the reaction heated under nitrogen overnight. TLC is used to monitor the reaction. Excess fluorophenol is added if necessary. The reaction is quenched with brine, and is extracted with $CH_2Cl_2$. The organic layer is washed three times with 1 N HCl, brine, dried ($Na_2SO_4$), and is concentrated. Without further purification, to this crude reaction mixture is added $CH_3CN$ and HF/Pyridine (0.1 mmol) while the flask is kept at 0° C. After 3 hours, at 0° C., the reaction is quenched with saturated aqueous NaCl. The aqueous layer is extracted three times with $CH_2Cl_2$, the organic layers combined and washed three times with 1 N HCl, brine, and dried ($Na_2SO_4$). After column chromatography (7:3, Hexane: Ethyl Acetate) the ester is obtained.

e.

13,14-dihydro-16,16 dimethyl, 16-(2-fluorophenoxy) tetranor prostaglandin F₁α

To a round bottom flask, 13,14-dihydro-16,16-dimethyl-16-(2-fluorophenoxy)-16-tetranor prostaglandin F₁α methyl ester and a 3:1 THF water mixture are added. The flask is cooled to 0° C., then an excess (2.5 equiv.) of lithium hydroxide is added, the ice bath removed, and the reaction is stirred at room temperature overnight. CH₂Cl₂ and saturated citric acid are added to the reaction mixture, the aqueous layer is washed 3 times with CH₂Cl₂, the organic layers are combined and is washed with brine, dried (Na₂SO₄), and chromatographed (CH₂Cl₂:methanol: acetic acid, 9.6: 0.4: 0.015 ). The acid 13,14-dihydro-16,16 dimethyl, 16-(2-fluorophenoxy) 16-tetranor prostaglandin F₁α is obtained.

Utilizing substantially the method of Example 1 (and using the appropriate starting materials), the following subject compounds of Examples 2–5 are obtained.

Example 2

13,14-dihydro-16,16,-dimethyl,16-(2-methylphenoxy)-16-tetranor Prostaglandin F₁α

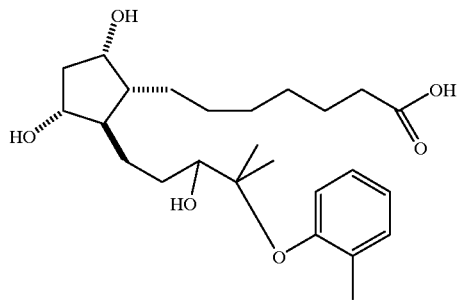

Example 3

13,14-dihydro-16,16,-dimethyl, 16-(2,3 difluorophenoxy-16-tetranor Prostaglandin F₁α

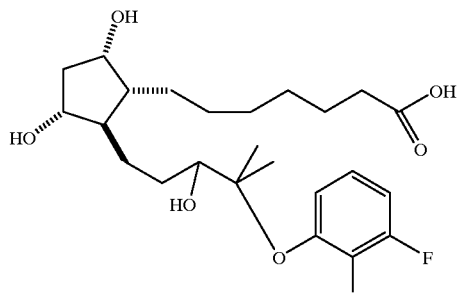

Example 4

13,14-dihydro-16,16,-dimethyl, 16-(2,5 difluorophenoxy)16-tetranor Prostaglandin F₁α methyl ester

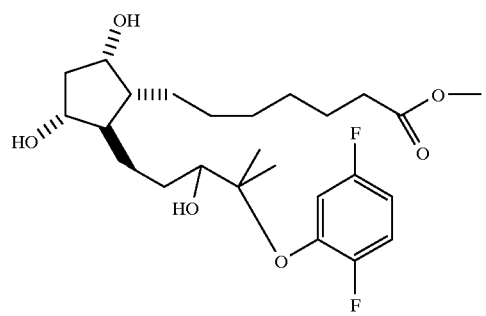

Example 5

13,14-dihydro-16,16,-dimethyl, 16-(3-fluoro-5-trifluoromethyl phenoxy) 16-tetranor Prostaglandin F₁α methyl ester

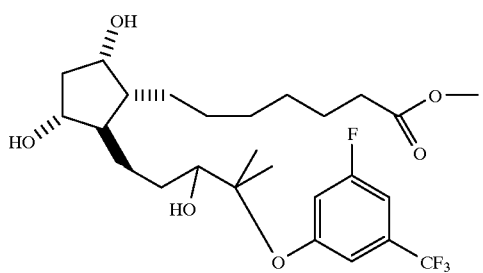

Example 6

Preparation of 13,14-dihydro-16,16-dimethyl, 16-(4-chlorophenoxy)-tetranor Prostaglandin F₁α

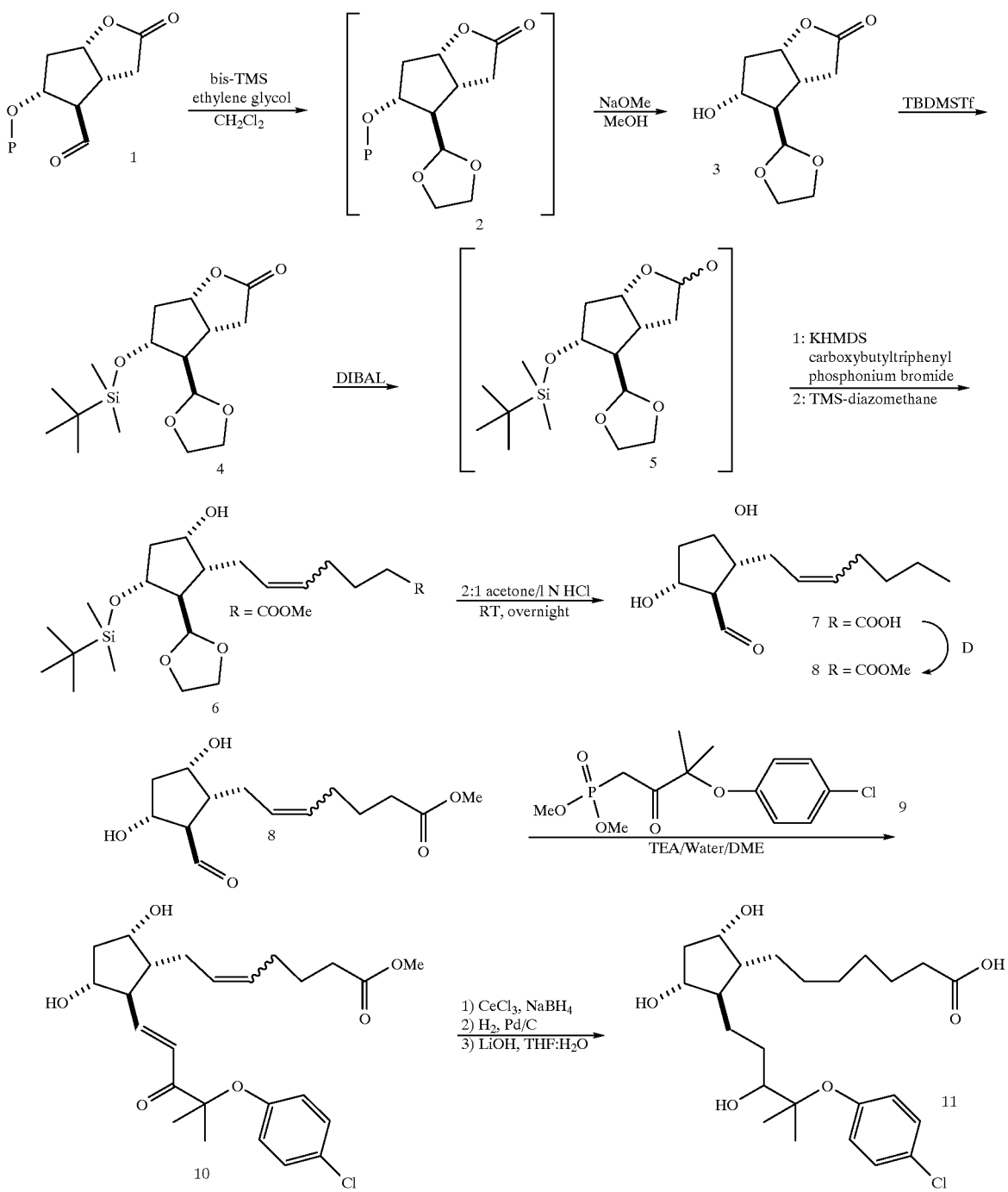

a.

6-(2,5-dioxolanyl)-7-hydroxy-2-oxabicyclo[3.3.0]octan-3-one

In a round bottom flask equipped with a magnetic stirbar is placed 1,2-bis(trimethylsilyloxy)ethane (1.3 eq.) in $CH_2Cl_2$ containing trimethysilyltrifluoromethanesulfonate at −78° C. To this is added, within 20 minutes, a solution of 1 (1 eq) in $CH_2Cl_2$. The reaction is stirred for 1 hour at −78° C. and then slowly warmed to 25° C. for 1 hour. The reaction is quenched at 0° C. with water, extracted with $CH_2Cl_2$ (3 times), dried ($MgSO_4$), and concentrated in vacuo to give crude 2. To a well stirred solution of crude 2 (1 eq) in methanol at 0° C. is added a suspension of sodium methoxide (1.2 eq) in MeOH. The reaction is stirred at 0° C. for 1 hour and then warmed to 25° C. for 1 hour. The reaction is neutralized with acidic ion exchange resin which is washed thoroughly with MeOH (5×). The filtrate is concentrated in vacuo to give a syrup which is subjected to flash chromatography on silica gel eluting with 4:1 hexane:ethyl acetate and 2% MeOH in $CH_2Cl_2$ to give 3.

b.

6-(2,5 dioxolanyl)-2-oxa-7-(1,1,2,2-tetramethyl-1-silapropoxy) bicyclo [3.3.0] octan-3-one In a round bottom flask with a magnetic stir bar, is stirred a solution of 3 (1 eq) in $CH_2Cl_2$. To this solution is added dropwise at −78° C. 2,6-lutidine (1.9 eq) followed by TBDMSOTf (1.8 eq). The reaction is stirred for 30 minutes at −78° C. and then warmed to 25° C. overnight. The reaction is quenched with water. The organic layer is washed with water (3 times), dried ($MgSO_4$), and concentrated in vacuo to give a yellow oil which is subjected to flash chromatography on silica gel (hexanes then 1% MeOH in $CH_2Cl_2$). The product is then washed with 1 N HCl (2 times), 0.1 N HCl (2 times), water, and brine to give 4.

c.

methyl 7-(5-(2,5-dioxolanyl)-2-hydroxy4-(1,1,2,2-tetramethyl-(1-silapropoxy) cyclopentyl)hept-5-enoate In a round bottom flask with a magnetic stir bar, is stirred a solution of 4 (1 eq) in dry toluene. To this solution, at −78° C., is slowly added DiBAL (1.24 eq). The reaction mixture is stirred for 2 hours and then warmed to 0° C. Saturated $NH_4Cl$ is added to the reaction mixture which is then slowly warmed to 25° C. Diluted with water, the insoluble precipitate is removed by suction filtration and the solid is washed with EtOAc (2 times). The liquid phase is extracted with EtOAc (3 times) and the combined organic phase is dried ($MgSO_4$) and concentrated in vacuo to give the product, 5. The product, 5, must either be used immediately or stored at −70° C. overnight.

To a suspension of (4-carboxybutyl) triphenylphosphonium bromide (2.2 eq) in THF at 0° C. under $N_2$ is added dropwise a solution of KHMDS (0.5 M KHMDS in toluene, 4.4 eq). The resulting deep orange color reaction mixture is stirred for 1 hour at 25° C. To the reaction mixture above at −78° C. is added a solution of 5 (1 eq) in THF. The reaction mixture is allowed to warm to 25° C. overnight. The reaction is quenched with water at 0° C. and the pH is adjusted to 3.5–4.0 with 1N HCl. The water phase is extracted with EtOAc (3 times) and the combined organic phase is dried ($MgSO_4$) and is concentrated in vacuo to give a syrup containing crude acid. To a well stirred solution of crude acid in ether and MeOH at 0° C. is added TMS-diazomethane until the reaction mixture keeps a light yellow color. The addition of 1 drop of glacial acetic acid and thin layer chromatography verifies that the reaction has gone to completion. The reaction solution is concentrated in vacuo and purified via flash chromatography on silica gel (30% EtOAc in hexanes) yielding 6.

d.

methyl 7-(2,4-dihydroxy-5-formylcyclopentyl)hept-5-enoate

In a round bottomed flask with a magnetic stir bar is placed an amount of the ketal, 6. To this flask is added a sufficient amount of a mixture of 2 parts acetone 1 part 1N HCl to bring the ketal completely into solution. This material is stirred until, by TLC, the starting material is consumed, typically overnight. The crude mixture containing the product 7 is extracted with ether and the ether extract esterified in situ with, preferably, TMS-diazomethane. This allows for the formation of the product 8, which is purified by column chromatography (30% EtOAc/hexanes) or is taken on without further purification.

e.

1-(dimethoxyphosphono)-3-(4-chlorophenoxy)-3-methyl butan-2-one

In a dry flask under $N_2$ is added THF (anhydrous) and Methyl dimethyl phosphonate (1 equiv.). The solution is cooled to −78° C. and nBuLi solution (1.1 eq, of 2.5 M solution in hexanes) is added dropwise and then is stirred for 1 hour. The ester of 2-(4-chlorophenoxy)-2-methyl propionic acid is added dropwise in THF. This is stirred overnight and is allowed to warm to room temperature. The crude mixture is quenched with saturated $NH_4Cl$, then extracted with $CH_2Cl_2$ and purified by flash chromatography (5% MeOH in $CH_2Cl_2$) to yield 9.

f.

16,16-dimethyl-16-(4-chlorophenoxy)-15-oxo-16-tetranor $PGF_2\alpha$ methyl ester In a round bottom flask equipped with a magnetic stirbar is placed 3-(2,4-dichlorophenoxy)-dimethyl-2-oxo-propylphosphonate (1.65 eq) in DME and water (30:1). To this solution is added lithium bromide (2 eq), triethylamine (5.30 eq), and methyl 7-(2-formyl-3,5-dihydroxycyclopentyl)hept-5-enoate (1.0 eq). The solution is stirred at room temperature for 24 hours. Ether is added and the solution is washed once with 0.1 N HCl, and brine. The organic layer is dried ($MgSO_4$), filtered, and concentrated under reduced pressure. Purification is effected by silica gel column chromatography (methanol/$CH_2Cl_2$ 1:50) to give 16,16-dimethyl-16-(4-chlorophenoxy)-15-oxo-16-tetranor $PGF_2\alpha$ methyl ester, 10.

g.

13,14-dihydro-16,16-dimethyl-16-(4-chlorophenoxy)-16-tetranor $PGF_1\alpha$

In a flame-dried round-bottomed flask equipped with a stir bar is placed 10 (1.0 equiv.), and cerium trichloride (1.05 eq) in methanol. The solution is stirred at room temperature for 5 minutes. The solution is cooled to −10° C. and sodium borohydride (1.02 eq) in methanol is added. The solution is stirred at −10° C. for 3 hours. The mixture is treated with water and the pH brought to ~6 with 1 N HCl. The mixture is extracted twice with ethyl acetate, and the organic layers combined, dried ($MgSO_4$), filtered and concentrated under reduced pressure. Purification is effected by silica gel column chromatography (3% methanol in $CH_2Cl_2$ to 5% methanol in $CH_2Cl_2$) to give the 15-(R) alcohol and the 15-(S) alcohol. In a flame-dried round-bottomed flask equipped with a stir bar is placed one or the other of the epimeric alcohols, or a mixture thereof (1.0 eq) and palladium on carbon (10% Pd on C) in ethyl acetate. The heterogeneous mixture is treated with hydrogen gas for 18 hours. The mixture is then filtered through Celite and concentrated under reduced pressure to give the title saturated prostaglandin as the methyl ester. In a round-bottomed flask equipped with a stir bar is placed said ester (1.0 eq) and lithium hydroxide monohydrate (1.8 eq) in a 50/50 THF water solution. The mixture is stirred at room temperature for 6 hours and then diluted with water and acidified to pH ~2–3 with 1 N HCl. The aqueous phase is extracted ~3 times with ethyl acetate and the organic layers combined. The combined organic layers are dried (MgSO$_4$), filtered, and concentrated under reduced pressure to yield 13,14-dihydro-16,16-dimethyl-16-(4-chlorophenoxy)-16-tetranor PGF$_1$α.

Utilizing substantially the method of Example 6 (and using the appropriate starting materials), the following subject compounds of Examples 7–14 are obtained.

Example 7

13,14-dihydro-16-methyl-16-(3-chlorophenoxy)-16-tetranor prostaglandin F$_1$α

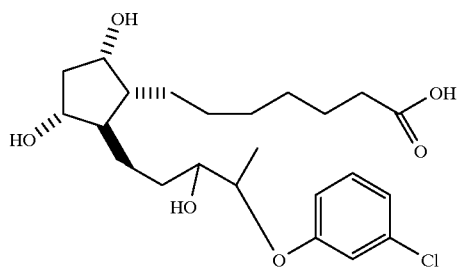

Example 8

13,14-dihydro-16-ethyl-16-(2-methylphenoxy)-16-tetranor Prostaglandin F$_1$α

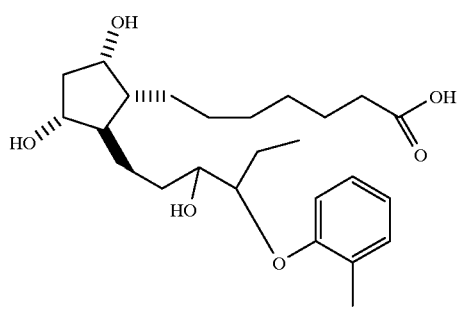

Example 9

13,14-dihydro-16-isopropyl 16-(2-fluorophenoxy)-16-tetranor Prostaglandin F$_1$α

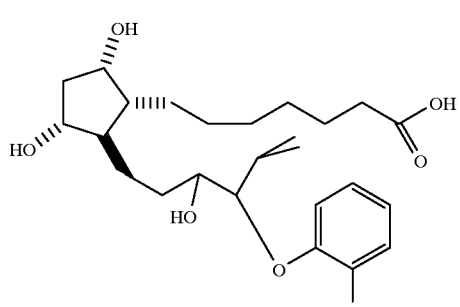

Example 10

13,14-dihydro-16-(hydroxymethyl)-16-phenoxy-16-tetranor Prostaglandin F$_1$α

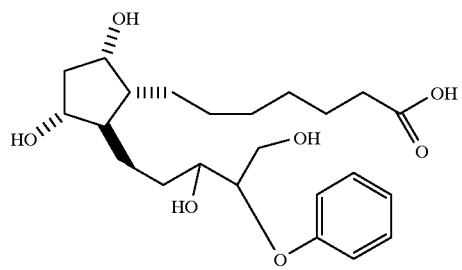

Example 11

13,14-dihydro-16-methyl-16-(4-ethylphenoxy)-16-tetranor Prostaglandin F$_1$α

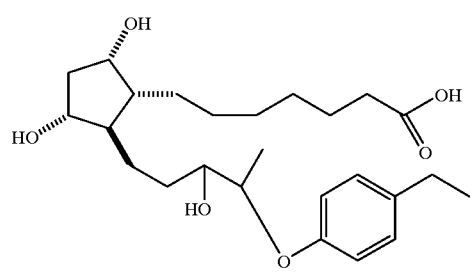

Example 12

13,14-dihydro-16-methyl-16-(3-chlorophenoxy)-16-tetranor prostaglandin F$_1$α methyl ester

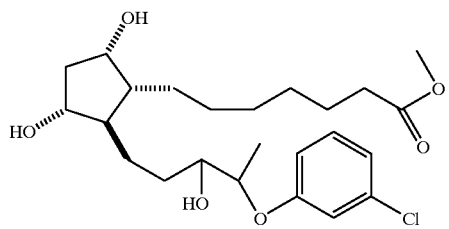

Example 13

13,14-dihydro-16-methyl-16-(4-phenylphenoxy)-16-tetranor prostaglandin $F_1\alpha$ isopropyl ester

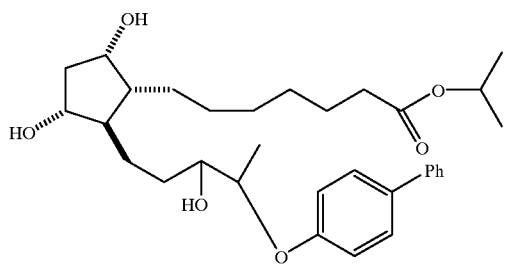

Example 14

13,14-dihydro-16,16-dimethyl-16-(4-phenoxyphenoxy)-16-tetranor prostaglandin $F_1\alpha$ isopropyl ester

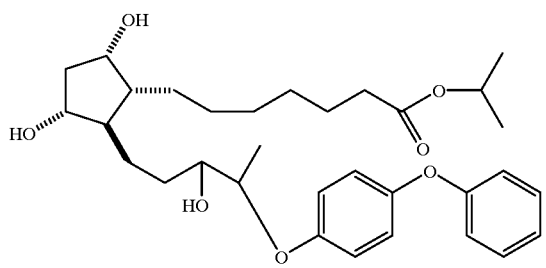

Example 15

Preparation of 13,14-dihydro-16,16-dimethyl-16-(2-fluorophenoxy)-16-tetranor Prostaglandin $F_{1a}$ hydroxamic acid

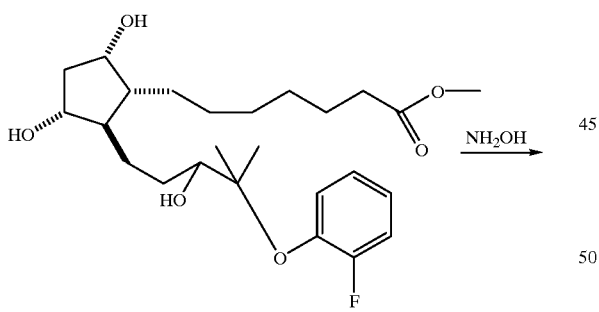

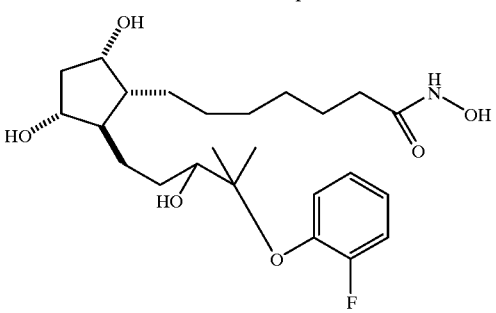

In a flame-dried round-bottomed flask equipped with a magnetic stir bar is placed 13,14-dihydro-16,16-dimethyl-16-(2-fluorophenoxy)-16-tetranor Prostaglandin $F_{1a}$ -methyl ester (Example 1) (1.0 equiv.) in methanol. To this solution is added hydroxylamine in methanol (1.25 equiv.) and the solution is stirred for 18 hours. The solution is treated with 1 N hydrochloric acid and extracted with ethyl acetate. The organic layer is washed with brine, dried ($MgSO_4$), filtered and concentrated under reduced pressure. The residue is purified by chromatography to give 13,14-dihydro-16,16-dimethyl-16-(2-fluorophenoxy)-16-tetranor Prostaglandin $F_{1a}$ hydroxamic acid.

The compounds of Examples 16–18 are prepared in a substantially similar manner as Example 15 using the appropriate hydroxylamine or sulfonamide and the intermediate corresponding to the appropriate example.

Example 16

13,14-dihydro-16-methyl-16-(3-chlorophenoxy) tetranor Prostaglandin $F_{1a}$ 1-hydroxamic acid

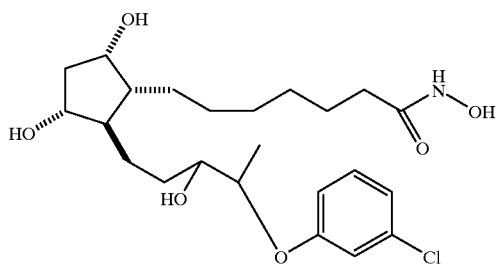

Example 17

13,14-dihydro-16-methoxymethyl-16-(2,3-difluorophenoxy)-16-tetranor Prostaglandin $F_{1a}$ 1-hydroxamic acid

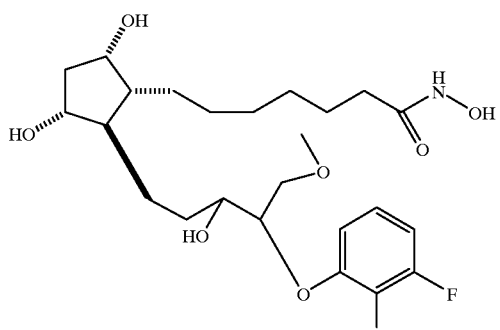

Example 18

13,14-dihydro-16-methyl-16-(3-methoxyphenoxy) tetranor Prostaglandin $F_{1a}$ 1-N-methanesulfonamide

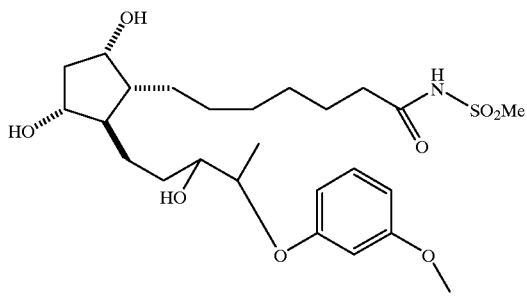

Example 19

Preparation of 13,14-dihydro-15-fluoro-16-(2-fluorophenoxy) tetranor Prostaglandin $F_{1a}$ methyl ester

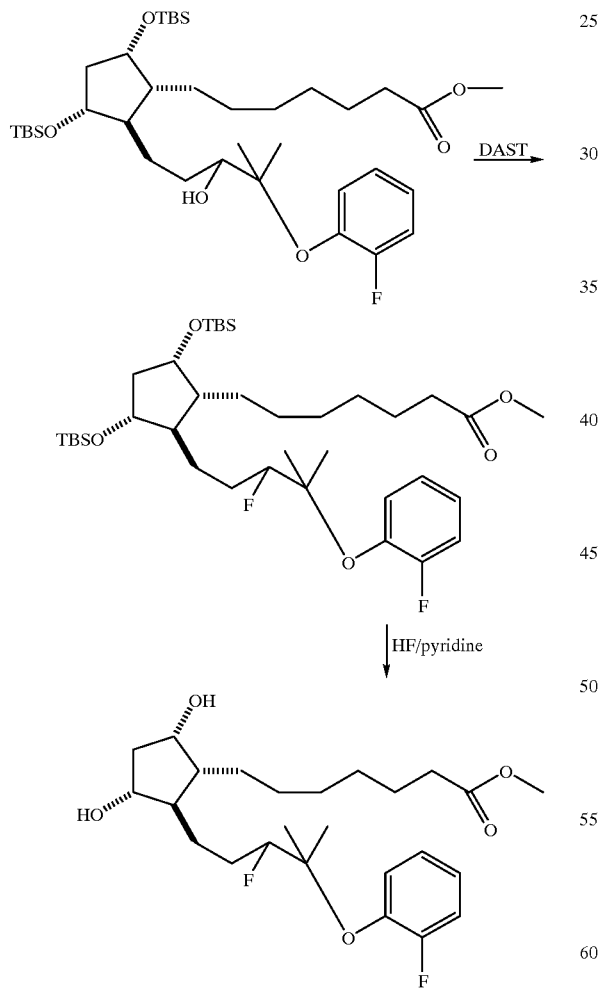

The bis-silyl ether of Example 1 is treated with diethylaminosulfur trifluoride (as disclosed in the following references: *Org. React.* Vol. 35 (1988) p. 513; *J. Org. Chem.* Vol. 40 (1975) p. 574; and references cited therein.) to give 13,14dihydro-15-fluoro-16-(2-fluorophenoxy) tetranor Prostaglandin $F_{1a}$ a methyl ester after deprotection as described in Example 1.

Utilizing substantially the method of Example 1 (and making the appropriate modification of $R_2$), the following subject compounds of Examples 20 and 21 are obtained.

Example 20

13,14-dihydro-15-methyl-16,16-dimethyl-16-(2-fluorophenoxy)-16-tetranor Prostaglandin $F_{1a}$

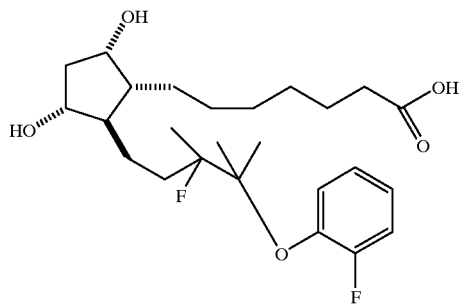

Example 21

13,14-dihydro-15-fluoro-16-(2,3-difluorophenoxy)-16-tetranor $PGF_{1a}$ 1-hydroxamic acid

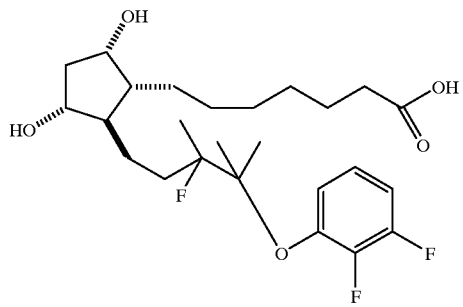

Example 22

Preparation of 13,14-dihydro-15-methylthio-15-dehydroxy-16-methyl-16-(2-methylphenoxy)-16-tetranor Prostaglandin $F_{1a}$

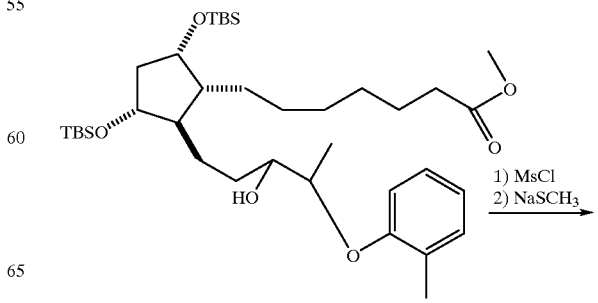

-continued

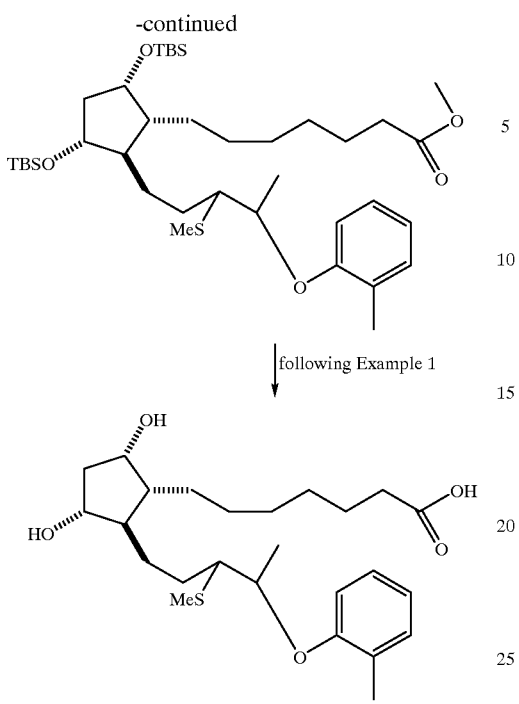

following Example 1

The appropriate bis-silylated compound synthesized as described in Example 1 is treated sequentially with methanesulfonyl chloride (1.2 equiv.) and base (1.2 equiv.) (as disclosed in the following references: *J. C. S. Chem. Comm.* (1975) p. 658; *Tetrahedron Lett.* (1975) p. 3183; and references cited therein.) to generate the intermediate mesylate which is then treated immediately with nucleophiles (sodium thiomethoxide) (as disclosed in *Tetrahedron Lett.* Vol. 23 (1982) p. 3463 and references cited therein.) to give the protected thioalkyl ether. Subsequent deprotection as described in Example 1 provides 13,14-dihydro-15-methylthio-15-dehydroxy-16-methyl-16-(2-methylphenoxy)-16-tetranor Prostaglandin $F_{1a}$.

Utilizing substantially the method of Example 22, the following subject compounds of Examples 23–25 are obtained.

Example 23

13,14-dihydro-15-methylthio-15-dehydroxy-16-methyl-16-(2-methylphenoxy) 16-tetranor Prostaglandin $F_{1a}$ 1-hydroxamic acid

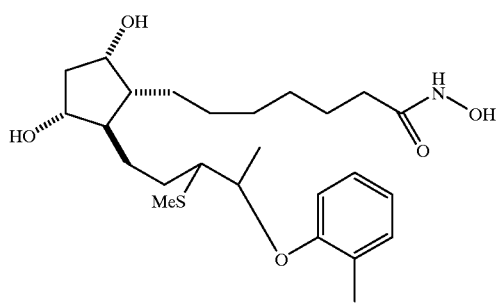

Example 24

13,14-dihydro-15-methoxy-16,16 dimethyl-16-(2-fluorophenyoxy) 16-tetranor Prostaglandin $F_{1a}$ hydroxamic acid

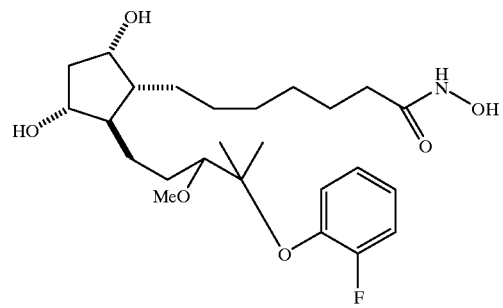

Example 25

13,14-dihydro-15-(ethoxy)-15-dehydroxy-16,16-dimethyl-16-phenoxy 16-tetranor Prostaglandin $F_{1a}$ methyl ester

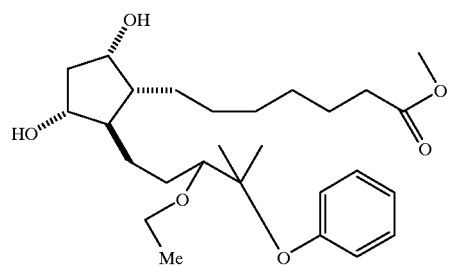

Example 26

Preparation of 13,14-dihydro-15-sulfonylmethyl-15-dehydroxy-16-methyl-16-(2-methylphenoxy)-tetranor Prostaglandin $F_{1a}$ methyl ester

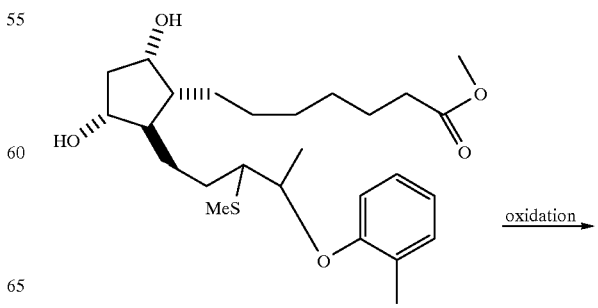

-continued

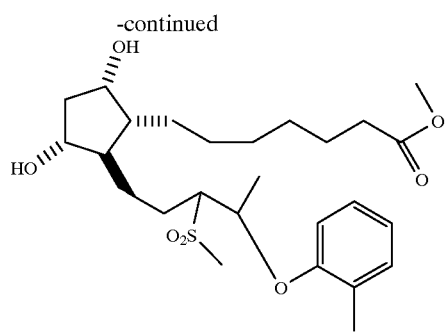

The methyl ester of Example 22 is treated with the appropriate oxidizing agent as disclosed in the following references: *Tetrahedron Lett.* (1982) p,3467; *Prostaglandins* Vol. 24 (1982) p. 801; Tetrahedron Lett. Vol. 23 (1982) p. 1023; and references cited therein.

Utilizing substantially the method of Example 26, the following subject compound of Example 27 is obtained.

Example 27

13,14-dihydro-15-sulfoxylmethyl-15-dehydroxy-16-methyl-16-(2-methylphenoxy)-16-tetranor Prostaglandin $F_{1a}$

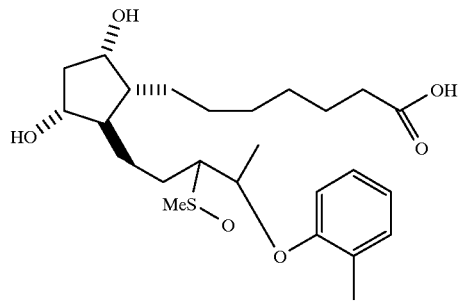

Example 28

Preparation of 13,14-dihydro-15-methyl-15-methylamino-15-dehydroxy-16,16-dimethyl-16-(2-fluorophenoxy)-16-tetranor Prostaglandin $F_{1a}$ methyl ester

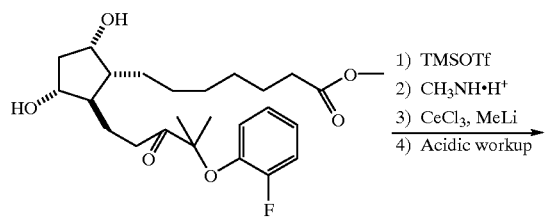

-continued

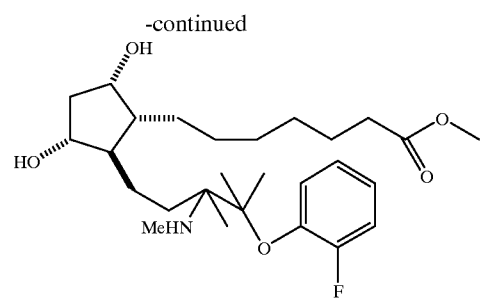

The appropriate intermediate from Example 2 is condensed with N-methylamine to give the imine. Addition of the methyl cerium nucleophile (~1.5 equiv.) (for examples of cerium chloride-mediated nucleophilic addition see: *J. Org. Chem.* Vol. 49 (1984) p. 3904; *J. Am. Chem. Soc.* Vol. 111 (1989) p. 4392; and references cited therein) gives the aminomethyl derivative, which is then transformed into 13,14-dihydro-15-methyl-15-methylamino-15-dehydroxy-16,16-dimethyl-16-(2-fluorophenoxy)-16-tetranor Prostaglandin $F_{1a}$ methyl ester.

Utilizing substantially the method of Example 28, the following subject compounds of Examples 29–31 are obtained.

Example 29

13,14-dihydro-15-methyl-15-methylamino-15-dehydroxy-16-methyl-16-(2-methylphenoxy)-tetranor Prostaglandin $F_{1a}$ 1-hydroxamic acid

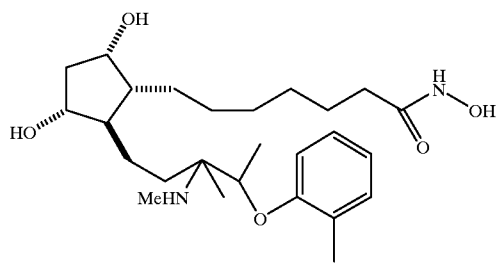

Example 30

13,14-dihydro-15-methyl-15-(N,N-dimethylamino)-16-ethyl-16-(2-fluorophenoxy)-16-tetranor Prostaglandin $F_{1a}$ isopropyl ester

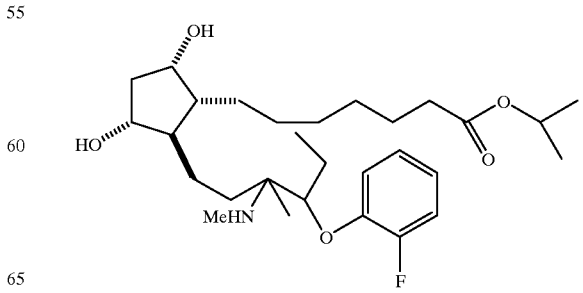

Example 31

13,14-dihydro-16-ethyl-16-(2,6-difluorophenoxy)-
16-tetranor Prostaglandin $F_{1\alpha}$ glyceryl ester

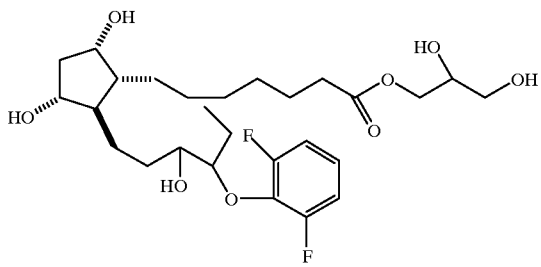

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing bone volume and trabecular number through formation of new trabeculae, increasing bone mass while maintaining a normalized bone turnover rate, and formation of bone at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 $\mu$g/kg body weight, preferably from about 0.1 to about 100 $\mu$g/kg per body weight, most preferably from about 1 to about 50 $\mu$g/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
| --- | --- |
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
| --- | --- |
| Compound of Example 1 | 5 mg |
| Phosphate buffered physiological saline | 10 mL |
| Methyl Paraben | 0.05 mL |

When 1.0 mL of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 14 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

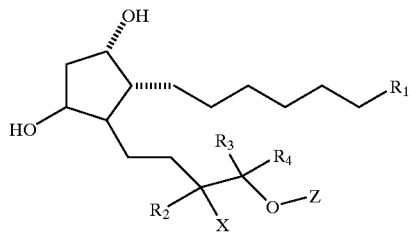

wherein
(a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;
(b) $R_2$ is H or lower alkyl;
(c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;
(d) $R_3$ and $R_4$ are independently H, alkyl, hydroxyalkyl, alkoxyalkyl, $OR_{10}$, or $SR_{10}$, except that both $R_3$ and $R_4$ are not H and when one of $R_3$ and $R_4$ is H, the other is not methyl; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;
(e) Z is carbocyclic aliphatic ring, heterocyclic aliphatic ring, aromatic ring, or heteroaromatic ring; and
any optical isomer, diastereomer, enantiomer of the above structure, or a pharmaceutically-acceptable salt, or biohydrolyzable amide, ester, or imide thereof.

2. The compound according to claim 1 wherein $R_1$ is selected from the group consisting of $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$.

3. The compound according to claim 2 wherein $R_2$ is H or $CH_3$.

4. The compound according to claim 3 wherein X is $OR_8$ or $NR_6R_7$.

5. The compound according to claim 4 wherein Z is monocyclic.

6. The compound according to claim 5 wherein Z is aromatic ring or heteroaromatic ring.

7. The compound according to claim 6 wherein Z is thienyl or phenyl.

8. The compound according to claim 7 wherein $R_1$ is selected from the group consisting of $CO_2H$, $C(O)NHOH$, $CO_2CH_3$, and $CO_2C_3H_7$.

9. The compound according to claim 8 wherein X is OH.

10. The compound according to claim 9 wherein Z is substituted, said substituents being independently selected from the group consisting of halo, alkyl, haloalkyl, cyano, alkoxy, phenyl, and phenoxy.

11. The compound according to claim 9 wherein Z is substituted, said substituents being independently selected from the group consisting of halo, alkyl, alkoxy, and phenyl.

12. The compound according to claim 9 wherein Z is substituted, said substituents being independently selected from the group consisting of halo, alkyl, and phenyl.

13. The compound according to claim 9 wherein said compound is selected from the group consisting of:
   13,14-dihydro-16,16-dimethyl 16-phenoxy 16-tetranor Prostaglandin $F_{1\alpha}$ methyl ester;
   13,14-dihydro-16,16-dimethyl 16-phenoxy 16-tetranor Prostaglandin $F_{1\alpha}$;
   13,14-dihydro-16-ethyl 16-phenoxy 16-tetranor Prostaglandin $F_{1\alpha}$ methyl ester;
   13,14-dihydro-16-ethyl 16-phenoxy-16-tetranor Prostaglandin $F_{1\alpha}$; and
   13,14-dihydro-16-hydroxymethyl 16-phenoxy tetranor Prostaglandin $F_{1\alpha}$ methyl ester.

14. A method of treating a human or other animal subject having a bone disorder, said method comprising administering to said subject a compound according to the structure:

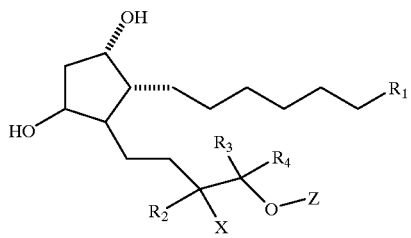

wherein
(a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;
(b) $R_2$ is H or lower alkyl;
(c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;
(d) $R_3$ and $R_4$ are independently H, alkyl, hydroxyalkyl, alkoxyalkyl, $OR_{10}$, or $SR_{10}$ except that both $R_3$ and $R_4$ are not H and when one of $R_3$ and $R_4$ is H, the other is not methyl; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;
(e) Z is carbocyclic aliphatic ring, heterocyclic aliphatic ring, aromatic ring, or heteroaromatic ring; and
any optical isomer, diastereomer, enantiomer of the above structure, or a pharmaceutically-acceptable salt, or biohydrolyzable amide, ester, or imide thereof.

15. The method of claim 14 wherein said bone disorder is osteoporosis.

16. The method of claim 15 wherein said bone disorder is post-menopausal.

17. The method of claim 15 wherein said bone disorder is osteoporosis is cortico-steroid induced.

18. The method of claim 14 wherein said bone disorder is osteopenia.

19. The method of claim 14 wherein said bone disorder is a bone fracture.

20. The method of claim 14 wherein said compound is administered orally.

21. The method of claim 14 wherein said compound is administered transdermally.

22. The method of claim 14 wherein said compound is administered intranasally.

23. A method of treating glaucoma, said method comprising administering to a human or other animal a safe and effective amount of a compound according to the structure:

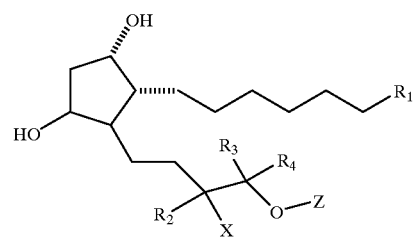

wherein
(a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;
(b) $R_2$ is H or lower alkyl;
(c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;
(d) $R_3$ and $R_4$ are independently H, alkyl, hydroxyalkyl, alkoxyalkyl, $OR_{10}$, or $SR_{10}$, except that both $R_3$ and $R_4$ are not H and one of $R_3$ and $R_4$ is H, the other is not methyl; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;
(e) Z is carbocyclic aliphatic ring, heterocyclic aliphatic ring, aromatic ring, or heteroaromatic ring; and any optical isomer, diastereomer, enantiomer of the above structure, or a pharmaceutically-acceptable salt, or biohydrolyzable amide, ester, or imide thereof.

24. The method of claim 23 wherein said compound is administered topically.

* * * * *

UNITED STATES PATENT AND TRADEMARK OFFICE
CERTIFICATE OF CORRECTION

PATENT NO.    : 6,048,895
DATED         : April 11, 2000
INVENTOR(S)   : John August Wos et al.

It is certified that error appears in the above-identified patent and that said Letters Patent is hereby corrected as shown below:

Column 30,
Line 63, delete "MeHN" and insert -- $Me_2N$ --.

This certificate supersedes the Certificate of Correction issued April 9, 2002.

Signed and Sealed this

Sixteenth Day of July, 2002

Attest:

Attesting Officer

JAMES E. ROGAN
Director of the United States Patent and Trademark Office